United States Patent [19]
Caldwell

[11] Patent Number: 5,462,540
[45] Date of Patent: Oct. 31, 1995

[54] TABLESS DIAPER WITH A MULTI-COMPONENT TAPE FASTENER

[75] Inventor: Carol A. Caldwell, Kirtland Hills, Ohio

[73] Assignee: Avery Dennison Corporation, Painesville, Ohio

[21] Appl. No.: 277,778

[22] Filed: Jul. 20, 1994

Related U.S. Application Data

[63] Continuation of Ser. No. 845,195, Mar. 2, 1992, abandoned.

[51] Int. Cl.⁶ ................................................. A61F 13/15
[52] U.S. Cl. ...................... 604/389; 604/358; 604/390; 604/385.1
[58] Field of Search ................................. 604/358, 386, 604/389, 390, 391, 385.1

[56] References Cited

U.S. PATENT DOCUMENTS

| | | | |
|---|---|---|---|
| 4,795,456 | 1/1989 | Borgers et al. | 604/389 |
| 4,801,480 | 1/1989 | Panza et al. | 604/390 |

FOREIGN PATENT DOCUMENTS

| | | | |
|---|---|---|---|
| 2035053 | 6/1980 | United Kingdom | 604/390 |

Primary Examiner—Paul B. Prebilic
Attorney, Agent, or Firm—Pearne, Gordon, McCoy & Granger

[57] ABSTRACT

Tabless adhesive fasteners are provided for diapers. In one aspect of the invention, one face of each adhesive fastener is permanently bonded to the diaper assembly proper at an associated permanent-bond area of the diaper assembly proper at one of the two lateral sides of the diaper assembly proper and adjacent the periphery of the diaper assembly proper. The other face of each adhesive fastener is releasably carried by liner or tape protective means carried on an area of the diaper assembly proper which is offset from such associated permanent-bond area. In another aspect of the invention, the adhesive fasteners include an adhesive layer which penetrates the water-permeable inner layer of the diaper assembly proper and adhesively interacts with the water-impermeable outer layer of the diaper assembly proper, whereby such adhesive layer and inner and outer diaper layers cooperate to provide a reinforced fastener base. Each adhesive fastener may comprise two adhesive layers with a carrier layer between them.

5 Claims, 1 Drawing Sheet

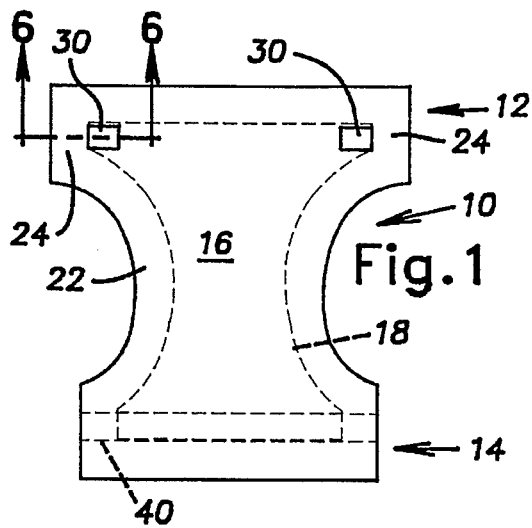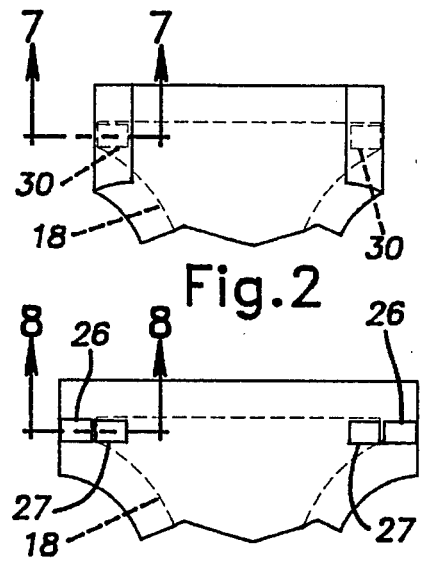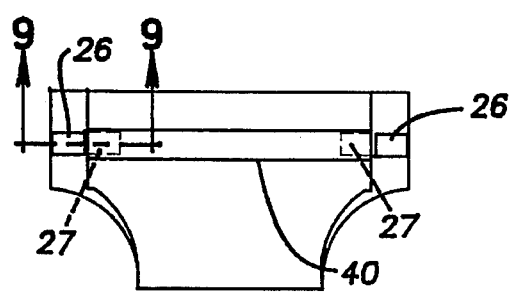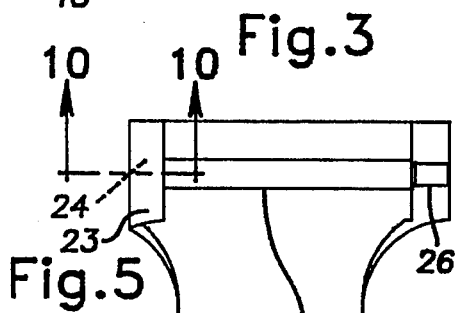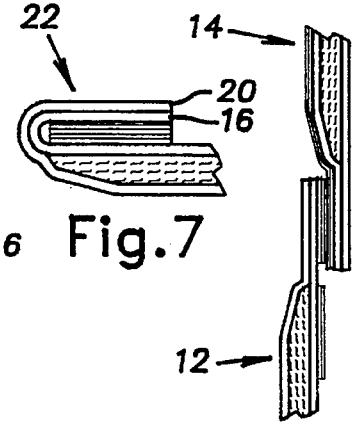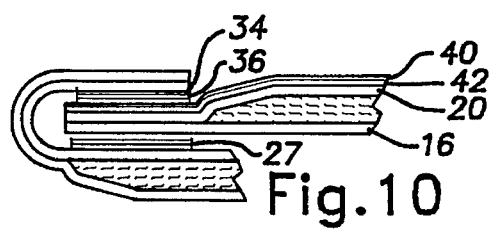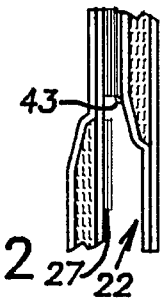

TABLESS DIAPER WITH A MULTI-COMPONENT TAPE FASTENER

This application is a continuation of application Ser. No. 07/845,195 filed Mar. 2, 1992, now abandoned in favor of the present case.

This invention relates to disposable diapers provided with self-contained adhesive fastener means for releasably fastening the diapers.

Diapers of this general kind are widely used. A successful type of diaper construction comprises an absorbent pad or batt or the like enclosed in an outer plastic shell of water-impermeable plastic film and an inner water-permeable shell or liner. The outer and inner shells are joined at a margin around the periphery of the diaper with the batt captured between them and spaced inwardly from the outer periphery. This construction may be referred to as the diaper assembly proper.

In such diaper assembly constructions, the absorbent batt is relatively thick and therefore bulky. Although materials of increased water absorbency have been developed to enable the bulk of the batt to be reduced, the batt remains relatively bulky as compared to the inner and outer shells.

Diapers of this general kind are provided with adhesive fastener means in the form of adhesive tabs fastened to one end of the diaper assembly construction at each lateral side of the diaper. The tabs have a face coated with pressure-sensitive adhesive. The tabs are releasably attachable to the other end of the diaper at each lateral side. The attachment is releasable both to allow permanent removal of the diaper and to allow unfastening to inspect the diaper followed by refastening if indicated.

In accordance with known practice, as illustrated for example in U.S. Pat. No. 4,753,649 to Pazdernik, the diaper may be provided at such other end with a stretch-resistant tab-receiving tape of polypropylene or other resin applied over the outer plastic shell both to reinforce the outer plastic shell (which may be relatively thin, stretchy, and prone to tearing) and to provide a smooth or matte peel-back release face to receive the sticky adhesive face of each tab when the tab is fastened. In a known manner, the release face and the pressure-sensitive adhesive of the tab are selected to give controlled release of the adhesive face from the tab-receiving tape, such that separation is strongly resisted when the tab is subject to lengthwise tensile loads as when the diaper is snugly wrapped and fastened around the wearer, but not when a tab end is peeled back from the tab-receiving face. Peelback occurs without tearing or stretching of the diaper or tab-receiving face. If desired, the adhesive face can be reclosed against the tab-receiving face to re-establish a strong bond. The relation wherein the tab strongly resists separation under tension but may be readily peeled back may be referred to as peelable bonding, and in this sense the tape may be said to be peelably bonded to the tab-receiving tape.

In general, the releasable fastening means of the prior art have comprised tabs fixed to the edges of the diaper at one end. The sticky adhesive face of each tab must be protected against contamination during storage and shipping of the diaper prior to use. In an early construction, the sticky face of each tab was protected with a piece of disposable release liner formed as the outer layer of the tab. When the diaper was applied, these small pieces were peeled off and thrown away. This was both inconvenient and environmentally undesirable because of the necessity of separately disposing of the small pieces of protective liner.

In current constructions, separate release liners are generally avoided. Instead, in the packaged and stored condition of the unused diapers, the adhesive tabs are stored in a position where they are folded back from the diaper edge, with the sticky adhesive face in releasable contact with a release means permanently bonded to the diaper. This self-storing release-liner arrangement avoids any need to dispose of separate small pieces of protective liner.

Efforts have been made to avoid the use of separate adhesive tabs altogether, and instead use adhesive areas on the diaper assembly proper.

In U.S. Pat. No. 2,649,848 to Le Bolt, diapers are provided with "self-sealing" adhesive which seals only to itself. Since the adhesive is self-sealing, the diaper is not readily reclosable because it cannot be readily opened without destroying or severely impairing the adhesive joint—the same joint that must be re-established to accomplish reclosing.

In U.S. Pat. No. 3,049,228 to Burnett, diaper-like paper towel stock is employed. Towel-like blanks or panels are provided with "mutually cohesive" adhesive which, similarly to Le Bolt, seals only to itself. The diaper-like construction cannot be reclosed and the arrangement does not lend itself to use with more successful types of disposable diaper constructions using absorbent batts between inner permeable linings and outer impermeable shells.

In U.S. Pat. No. 3,554,195 to Murdoch, adhesive areas on the diaper assembly proper are provided, each protected by a piece of separately removable liner. This arrangement is not self-storing in respect of the release liner, and has the disadvantages mentioned above in respect of separate small pieces of liner requiring separate disposal.

In U.S. Pat. No. 3,638,351 to Torr, adhesive areas and release liners are provided on the diaper assembly proper. However, this is done by direct coating of both the adhesive layers and release layers. These steps would be costly and difficult to implement on a diaper manufacturing line. The adhesive faces are not peelably bonded at the closure joints, and the diapers are not reclosable as disclosed. The first embodiment relies on adhesive-to-adhesive contact for closure. In other embodiments, fastening depends on bringing patches of pressure-sensitive adhesive coated on the outer diaper shell into adhering contact with the water-permeable body-contacting layer. This may result in weak bonds which are prone to readily tear, and which do not perform satisfactorily as reclosable joints.

In U.S. Pat. No. 3,840,013 to Mesek, adhesive areas are provided at marginal portions of the diaper assembly proper by direct coating onto the inner diaper layer, some of the adhesive soaking through to the outer diaper layer. Alternatively, double-face tape is applied to the inner diaper layer at the marginal portions. In both alternatives, as in Murdoch, the adhesive areas are protected by separate pieces of release liner, so that the arrangement is not self-storing in respect of liner, and requires separate disposition of the small pieces of protective liner. Also the adhesive faces are not peelably bonded at the closure joints, and the diapers are not reclosable as disclosed.

In U.S. Pat. No. 3,971,380 to Tritsch, again adhesive areas are provided at marginal portions of the diaper assembly proper and in structural association with both the inner and outer diaper layers. However again, as in Murdoch, the adhesive areas are protected by separate pieces of release liner, so that the arrangement is not self-storing in respect of liner, and requires separate disposition of the small pieces of protective liner.

In U.S. Pat. No. 4,985,025 to Lingertat et al., the diaper assembly proper is modified by extending the outer shell of the diaper assembly proper beyond the inner shell to provide "ears" or "flaps" of the outer shell of thin, stretchy, water-impervious material. A pressure-sensitive adhesive is permanently bonded to these ears to provide a sticky fastening face. In one embodiment, in the storage position, the sticky fastening face of each ear is carried on a release carrier bonded to the inner shell. The result is a self-storing release liner arrangement, but certain drawbacks are present. The ear relied on as a fastening tab functions poorly as a fastening tab because it consists of the outer shell material which is relatively thin and subject to stretching and tearing. In another embodiment, the release liner is also carried on the ear of outer shell material. Again, the ear functions poorly as a fastening tab for the same reasons as apply to the first embodiment. Moreover, the release liner either requires separate disposal or half of the sticky fastening face remains permanently covered by the release liner, further reducing the fastening effectiveness of the tab.

THE PRESENT INVENTION

The present invention provides a tabless diaper construction which overcomes the disadvantages of the prior art discussed above. The construction readily lends itself to current diaper manufacturing operations. Diapers are fastened securely, and may readily reopened and reclosed. The construction is self-storing in respect of release liner.

BRIEF DESCRIPTION OF THE DRAWINGS

In one aspect of the invention, one face of each adhesive fastener is permanently bonded to the diaper assembly proper at an associated permanent-bond area of the diaper assembly proper at one of the two lateral sides of the diaper assembly proper and adjacent the periphery of the diaper assembly proper. The other face of each adhesive fastener is releasably carried by liner or tape protective means carried on an area of the diaper assembly proper which is offset from such associated permanent-bond area. In another aspect of the invention, the adhesive fasteners include an adhesive layer which penetrates the water-permeable inner layer of the diaper assembly proper and adhesively interacts with the water-impermeable outer layer of the diaper assembly proper, whereby such adhesive layer and inner and outer diaper layers cooperate to provide a reinforced fastener base. Each adhesive fastener may comprise two adhesive layers with a carrier layer between them.

The objects and advantages of the invention will be more fully understood from the following description of specific embodiments, taken together with the accompanying drawings, in which:

FIG. 1 is a schematic sketch of a diaper and fastener embodying the invention at a stage of manufacture and use.

FIG. 2 is a schematic sketch of a diaper and fastener embodying the invention at a stage of manufacture and use.

FIG. 3 is a schematic sketch of a diaper and fastener embodying the invention at a stage of manufacture and use.

FIG. 4 is a schematic sketch of a diaper and fastener embodying the invention at a stage of manufacture and use.

FIG. 5 is a schematic sketch of a diaper and fastener embodying the invention at a stage of manufacture and use.

FIG. 6 is a cross-sectional view taken alone line 6—6 of FIG. 1.

FIG. 6A shows a detail of FIG. 6.

FIG. 7 is a cross-sectional view taken alone line 7—7 of FIG. 2.

FIG. 8 is a cross-sectional view taken alone line 8—8 of FIG. 3.

FIG. 9 is a cross-sectional view taken alone line 9—9 of FIG. 4.

FIG. 10 is a cross-sectional view taken alone line 10—10 of FIG. 5.

FIG. 11 is a view similar to FIG. 10 but on a reduced scale, showing the same elements in the same topological relationship, but better suggesting the relative positions of the parts in actual use.

FIG. 12 is a view similar to FIG. 11, still better suggesting the relative positions of the parts in actual use.

DETAILED DESCRIPTION OF THE INVENTION

While the present invention is specifically described in connection with the diapering of infants, it will be understood that it is also applicable to diapering of incontinent adults.

Shown in the drawings is a diaper 10. According to known practice, the diaper assembly proper has first and second ends 12 and 14 and comprises a moisture-pervious inner layer 16 of flexible nonwoven fabric or the like adapted to be positioned against the wearer's body, an absorbent pad or batt 18 adjacent the inner layer 16, and a moisture-impervious outer layer 20 of plastic film such as polyethylene or the like adjacent to the absorbent batt 18. (To simplify the drawings, the batt 18 is not shown in FIGS. 4 and 5.)

As shown, the inner and outer layers 16 and 20 have an hour-glass configuration. As also shown, the batt 18 may also have an hour-glass configuration, although in many cases it is preferred for the batt to have a substantially rectangular configuration. In any event, the two lateral sides of the assembly are spaced further apart at each diaper end than at the diaper center. The inner and outer layers 16 and 20 are secured to one another laterally outwardly of the absorbent batt 18 to provide at the periphery of the configuration a flexible two-layer battless diaper margin 22. The width of this margin is shown as approximately uniform along the lateral sides of the diaper, but when the batt is rectangular in shape, this margin at each lateral side of the diaper will be considerably wider at the ends of the diaper than it is at the central portion thereof.

At the stage of manufacture illustrated in FIGS. 1 and 6, fastener-receiving or permanent bond areas 24 at each lateral side of the first end 12 of the diaper assembly have yet to receive the adhesive fastening means contemplated by the invention. Preferably, the fastening means is a double-coated adhesive fastener assembly 26. During manufacture, each fastener assembly 26 may be initially applied to the diaper not at the fastener-receiving or permanent bond areas 24, but rather at adjacent areas inboard of the latter areas, each assembly 26 being applied in combination with a self-storing release liner 27.

Each self-storing release liner may comprise a base layer 27a provided with a release coat 28 of silicone or the like, and may be permanently adhered to the layer 16 by a suitable adhesive such as pressure-sensitive adhesive 29. The combined fastener assembly 26 and release liner 27 may be applied as a single unitarily-applied multi-component tape 30 consisting of all the tape elements seen in FIG. 6. This multicomponent tape may be applied using conventional tape or label application practices. Use of such tape lends itself well to established diaper manufacturing procedures.

Each double-coated adhesive fastener assembly 26 may include a carrier 32 of polypropylene film or nylon scrim or the like, and first and second adhesive layers 34 and 36 in permanently bonded relationship to the carrier 32. The transfer of each fastener assembly 26 to its associated fastener-receiving area 24 is initiated by folding a marginal portion of the diaper inwardly as seen in FIGS. 2 and 7, thus bringing the first adhesive layer 34 into contact and permanently bonded relation with the diaper margin at the permanent bond area 24.

In the illustrated construction, the exterior faces of the adhesive layers 29 and 34 will be seen to constitute two exterior faces presented by the multi-component tape 30 prior to its application to the diaper, one (the exterior face of layer 34) being associated with the adhesive means 26 and the other (the exterior face of layer 29) being associated with the release liner 27.

When the multi-component tape is fully applied as seen in FIGS. 2 and 7, these two exterior faces are seen to be applied to two adjacent areas of the inner face of the diaper (face of inner layer 16); such two areas will be seen to be the fastener-receiving area 24 and the (un-numbered) area of permanent bond between the release liner 27 and the diaper.

Thus, as to each lateral side of the diaper, it will be seen that the unitary application of the single multi-component tape as described comprises applying one of the two exterior faces of the multi-component tape to one of the aforesaid two adjacent areas of the inner face of the diaper, and folding the diaper around the described hinge line to thereby apply the other of the two exterior faces of the multi-component tape to the other of the aforesaid two adjacent areas of the inner face of the diaper.

Thus it is seen that during diaper manufacture, only a single tape, formed as a unitarily-applied multi-component tape comprising both fastener means and protective release liner, need be applied at each lateral side of the diaper to provide each side with protectively-stored adhesive fastening means. As will be described below, the protectively-stored fastening means provided by the single tape is adapted for deployment by releasing the fastening means from the release liner.

While the schematic drawings show the adhesive layer 34 merely contacting the moisture-permeable inner layer 16 of the diaper, this latter layer is actually a flexible nonwoven fabric or the like which is penetrated by the adhesive, and whose fibers are enveloped and captured by the adhesive. The penetrating adhesive 34 also adhesively interacts with or adheres to the outer layer or shell 20. The adhesive 34 and the layers 16 and 20 thus cooperate at the fastener-receiving area 24 to provide a reinforced fastener base at this area. The adhesive 34 may be selected to have desired rheological and adhesive properties for these purposes. The following formulation by weight percent may be used for the adhesive layer 34:

| | |
|---|---|
| Kraton 1117 (Shell Chemical) | 42.0 |
| Escorez 131OLC (Exxon Chemical) | 35.0 |
| Herculyn D (Hercules) | 11.0 |
| Foral 85 (Hercules) | 10.0 |
| Ethanox 330 (Ethyl) | 1.0 |
| Plastonox LTDP (American Cyanimid) | 1.0 |

This same formulation may be used for the adhesive layer 29.

The diapers may be packaged in groups of, say, ten or twenty or more for shipment and sale in the configuration just described, with the marginal edges folded inwardly as shown in FIGS. 2 and 7. Each diaper is folded end-on-end in a manner similar to the end-on-end folding seen in FIGS. 4 and 5. In this configuration shown in FIGS. 2 and 7, the entire multicomponent tape 30, including the fastener assembly 26 together with the layers 27–29, remains together. At this stage, the adhesive layer 29 of the release liner remains permanently associated with the inner diaper liner 16, the first adhesive 34 of the fastener assembly 26 remains permanently associated with the diaper margin 22 in the manner described, and the face of the second adhesive layer 36 remains in protected condition in contact with the release coat 28 of the release liner 27.

In accordance with known practice, and as previously described above, when conventional adhesive tabs are used, it is known to provide a tab-receiving tape applied over the outer plastic shell both to reinforce the outer plastic shell and to provide a peel-back release face to receive the sticky adhesive face of each tab when the tab is fastened. In a known manner, the pressure-sensitive adhesive of the tab is selected to give controlled release of the adhesive face from the tab-receiving tape, such that separation is strongly resisted when the tab is subject to lengthwise tensile loads as when the diaper is snugly wrapped and fastened around the wearer, but not when a tab end is peeled back from the tab-receiving face. The present invention may also use such a tape, but instead of receiving tabs it receives the fastener assemblies 26. A fastener-receiving tape 40 of polypropylene or the like may be provided, heat-sealed or adhered as by adhesive layer 42, to the diaper's outer layer 20 near the second or front diaper end 14, and positioned to receive the adhesive face 34 of each adhesive fastener assembly 26 when the diaper is closed, as described below. The tape 40, if employed, may include a release coating of silicone or the like or, as shown, the tape may include no release coating as such.

When a fastener-receiving tape 40 of polypropylene or the like is employed, the following formulation by weight percent may be used for the adhesive layer 36:

| | |
|---|---|
| Kraton 1107 (Shell Chemical) | 31.7 |
| Escorez 131OLC (Exxon Chemical) | 46.3 |
| Wingtack 10 (Goodyear Chemical) | 19.8 |
| Ethanox 330 (Ethyl Corp.) | 1.0 |
| Plastonox LTDP (American Cyanimid) | 1.2 |

The same formulation may be used for an adhesive to adhere the tape 40 to the moisture-impervious outer layer 20 of polyethylene or the like.

When a fastener-receiving tape 40 is not employed, the following formulation may be used for the adhesive layer 36, which directly engages the moisture-impervious outer layer 20 of polyethylene or the like:

| | |
|---|---|
| Kraton 4141 (Shell Chemical) | 42.3 |
| Piccolyte A-115 (Hercules) | 39.1 |
| Kristalex 1120 (Hercules) | 6.2 |
| Herculyn D (Hercules) | 10.4 |
| Ethanox 330 (Ethyl Corp.) | 1.0 |
| Plastanox LTDP (American Cyanimid) | 1.0 |

When the diaper is to be applied to a baby, it is removed from its packaging and the marginal edges that were folded inwardly are unfolded, thereby peeling the adhesive 36 from the release liner 27 and completing the transfer of each fastener assembly 26 to its associated fastener-receiving area 24, as seen in FIGS. 3 and 8. The diaper is folded between the baby's legs in the usual manner so that the ends 12 and 14 wrap around the back and front of the baby's waist and meet at the sides. A flattened version of this condition of the diaper is seen in FIGS. 4 and 9. If desired, the diaper may be placed on the baby before the marginal edges are unfolded, and in general this will be the preferred sequence because the face of the adhesive 36 remains protected during the time the diaper is being placed on the baby. In other words, before the marginal edges are unfolded from the condition seen in FIGS. 2 and 7, the diaper itself can be unfolded and placed on the baby and refolded to cover the baby's crotch, with the first end 12 of the diaper covering the back of the baby's waist and the second end 14 covering the front of the baby's waist. The diaper margins are then unfolded to the condition seen in FIGS. 3, 4, 8 and 9 to expose the face of the adhesive layer 36 (i.e., to deploy the fastening means 26). The diaper is then fastened by placing the opened marginal portions over the ends of the fastener-receiving tape 40 to apply the adhesive face 36 of each fastener assembly against the tape. This fastened condition is shown at the left side of FIG. 5 and in FIG. 10. FIG. 11 is similar to FIG. 10 and shows the same elements in the same topological relationship, but better suggests the relative positions of the parts of one of the fasteners when the diaper is positioned on the baby and closed and fastened at each side of the baby's waist. The baby's waist would be to the right as the closure is viewed in FIG. 11. The parts as seen in FIG. 11 shown as flat for simplicity of illustration, but in actuality would of course tend to follow the curvature of the baby's waist.

FIG. 12 even better suggests the relative positions of the parts when the diaper is on a baby, since it is not likely, when the diaper is applied and snugged around the baby, that the adhesive face 36 will be applied against the portion of the fastener-receiving tape 40 which overlies the margin 22 at the second end 14. Rather, it will be natural for the person applying the diaper to apply the face 36 to portions of the tape 40 somewhat nearer the lateral center of the diaper, as shown in FIG. 12. It may therefore be preferred to eliminate the portions of the fastener-receiving tape ends which overlie the margin 22 at each side of the diaper at the second end 14, so that the tape 40 terminates at each of its ends short of the margin 22. FIG. 12 shows this alternative, the fastener-receiving tape being shown as terminated at end 43, short of the associated margin portion 22 of the diaper. Again, in actuality the parts would not be flat as shown, but would follow the curvature of the baby's waist.

As with the tabs of the prior art used with tab-receiving tapes, the adhesive 36 is selected to give controlled release of the adhesive face from the fastener-receiving tape 40. This controlled release is such that separation is strongly resisted when the tab is subject to lengthwise tensile loads, as when the diaper is snugly wrapped and fastened around the wearer, or when it is stressed by movements of the wearer, but not when the fastener assembly 26 and the portion of the margin 22 to which it is permanently adhered are peeled back from the fastener-receiving face of the tape 40 to open the fastening. A peelback grip for starting the peeling action is provided by the portions of the margin 22 immediately to the side of the fastener-receiving areas 24, such as the margin portion labelled 23 in FIG. 5.

Peelback occurs without significant tearing or stretching of the relatively fragile shell 16 or of the fastener-receiving face of the tape 40, and the fastening is thereby opened, as illustrated at the right side of FIG. 5 as to one side of the diaper. At this point the diaper can be discarded after opening both sides, or the diaper can be inspected and reclosed. To reclose, the exposed adhesive face of the opened fastener assembly 26 can be reclosed against the tape 40 to re-establish a strong bond. Again, when the diaper is to be removed or reinspected, this strong bond can be broken by peeling back as previously described.

The relation wherein the fastener assembly 26 strongly resists separation under tension but may be readily peeled back provides peelable bonding as referred to above, and matches the performance of prior-art adhesive fastening tabs in this regard.

Instead of providing the multicomponent tape 30 including the special release liner 27, when a fastener-receiving protective tape 40 is employed, the adhesive fastener assembly 26 may be combined with the tape 40 at the factory to provide a flattened and folded construction similar in appearance to that seen in FIGS. 5 and 10 (but of course without the release liner 27 and associated elements 28 and 29), or similar in appearance to that of a flattened and folded construction corresponding to the unfolded construction seen in FIG. 12 (again, without the release liner 27 and associated elements 28 and 29).

This may be accomplished by directly applying a pair of double-coated adhesive fastener assemblies to the fastener-receiving areas at the first end 12 of the diaper, applying the tape 40 to the second end 14 of the diaper, and folding the diaper and the margins at the first end 12 to bring the ends of the diaper together and close both sides of the diaper to the flattened condition similar to that shown at the left side of FIG. 5. A number of diapers configured in such flattened and closed condition can be packaged together for shipment and sale.

In the left side of FIG. 5, the leftmost vertical line in the drawing will be seen to be the hinge line around which the diaper is wrapped, in the vicinity of the associated fastener-receiving area 24, when the diaper is in such flat and closed condition.

While it is preferred to provide a double-coated adhesive fastener assembly 26 as described above for each side of the diaper, it is also contemplated that the fastener 26 be replaced by an adhesive fastening means comprising a single adhesive layer in place of the layers 34 and 36, in which case the carrier 32 is eliminated. Such single-adhesive-layer fastener may be combined with the release liner 27 to be transferred therefrom in a manner similar to that described for the double-coated fastener assembly 26. The reinforcing effect of the carrier is not present in such construction, but the single adhesive layer penetrates the inner diaper layer 16 of flexible nonwoven fabric or the like whose fibers are enveloped and captured by the single adhesive layer. The single adhesive layer adhesively interacts with the outer layer or shell 20, so that the single adhesive layer and the layers 16 and 20 cooperate to provide a reinforced fastener base in the manner previously described in connection with adhesive layer 34.

Alternatively, such single adhesive layer may be transfer-applied to and combined with the tape 40 at the factory in a manner similar to the combining of the multicomponent tape 30 as described above, thus eliminating use of a special release liner such as liner 27.

Where the fastener-receiving tape is not provided to act as the peel-back release-face means against which the face of adhesive layer 36 (or the face of a single-adhesive-layer fastening means) is releasably adhered when the diaper is fastened on a baby, the moisture-impervious outer liner or layer 20 of the diaper proper may perform such function and act as the peel-back release-face means. In cases where neither the release liner 27 nor the fastener-receiving tape 40 is provided and therefore neither is available to act as protective means for the face of adhesive layer 36 (or for the face of a single-adhesive-layer adhesive fastening means), the moisture-impervious outer liner or layer 20 may also function as such protective means against which the face of the adhesive fastening means is releasably adhered to be protected during shipment and storage.

It should be evident that this disclosure is by way of example, and that various changes may be made by adding, modifying or eliminating details without departing from the fair scope of the teaching contained in this disclosure. The invention therefore is not limited to particular details of this disclosure except to the extent that the following claims are necessarily so limited.

What is claimed is:

1. A tabless adhesively-fastenable disposable diaper including a diaper assembly proper having first and second ends and an inner face and an outer face and comprising a moisture-pervious inner layer adapted to be positioned adjacent a wearer's body, an absorbent batt adjacent to said inner layer, and a moisture-impervious outer layer adjacent to said absorbent batt, said inner and outer layers of said diaper assembly having a generally hour-glass configuration and being larger than said absorbent batt and secured to one another outwardly of said absorbent batt to provide at the periphery of said configuration a flexible two-layer battless diaper margin including fastener-receiving areas on said inner face at each lateral side of the first end of said diaper assembly, an adhesive fastening means associated with each lateral side of said first end of said diaper assembly proper, each said adhesive fastening means being permanently bonded on said inner face to one of said fastener-receiving areas, each said adhesive fastening means being adapted to be releasably carried by protective means, said protective means comprising combined fastener-receiving and protective tape means permanently bonded to portions of the diaper assembly proper at the second end of the diaper and on said outer face, said diaper being configured for shipment and sale in a folded configuration with its first and second ends releasably adhered by said carrying of said adhesive fastening means by said combined fastener-receiving and protective tape means, the diaper, in said folded configuration, being wrapped around hinge lines, in the vicinities of said fastener-receiving areas.

2. A device as in claim 1, each said adhesive fastening means being a double-coated adhesive fastener assembly including a carrier and first and second adhesive layers in permanently bonded relation to said carrier.

3. A tabless adhesively-fastenable diaper including a diaper assembly proper having first and second ends and an inner face and an outer face and comprising a moisture-pervious inner layer adapted to be positioned adjacent a wearer's body, an absorbent batt adjacent to said inner layer, and a moisture-impervious outer layer adjacent to said absorbent batt, said inner and outer layers of said diaper assembly being larger than said absorbent batt and secured to one another outwardly of said absorbent batt to provide at the periphery of said configuration a flexible two-layer battless diaper margin, an adhesive fastening means associated with each lateral side at one end of said diaper assembly proper, each said adhesive fastening means being permanently bonded to said diaper assembly proper on said inner face thereof at an associated permanently bonded area at one of the two lateral sides of said diaper assembly proper and within said two-layer battless portion of said diaper assembly proper, each said adhesive fastening means comprising adhesive layer means including an adhesive layer which penetrates said moisture-pervious diaper inner layer and adhesively interacts with said moisture-impervious diaper outer layer whereby said adhesive layer and said inner and outer diaper layers cooperate to provide a reinforced fastener base, said adhesive layer means of each said adhesive fastening means further including an adhesive face adapted to be releasably adhered in protected relation to protecting means at a portion of said diaper assembly proper other than said associated permanently bonded area.

4. A device as in claim 3, in which said protection means to which said adhesive face is releasably adhered in protected relation comprises a release liner associated with each said adhesive fastening means, each said release liner being permanently bonded to said diaper assembly proper on said inner face thereof at an area on said diaper assembly proper adjacent to and laterally inward of said previously recited permanently bonded area, said diaper being configured for shipment and sale in a folded configuration with said protected adhesive face of each said adhesive fastening means being in protected releasably-carried relation with said release liner.

5. A device as in claim 3, in which said protection means to which said adhesive face is releasably adhered in protected relation comprises tape means permanently bonded on said outer face of said diaper assembly proper to portions of the diaper assembly proper on the opposite end of the diaper from the end with which said adhesive layer means are associated, said diaper being configured for shipment and sale in a folded configuration with said adhesive face of each said adhesive layer means being in said protected releasably-carried relation with said tape means, the diaper, in said folded configuration, being wrapped around hinge lines, in the vicinities of said permanently-bonded areas, that are closer to lengthwise of the diaper than transverse to it.

* * * * *